United States Patent
Nehls

(10) Patent No.: US 9,750,513 B2
(45) Date of Patent: Sep. 5, 2017

(54) SPINAL MARKER SYSTEM AND METHODS OF USE

(71) Applicant: Daniel Nehls, Tacoma, WA (US)

(72) Inventor: Daniel Nehls, Tacoma, WA (US)

(*) Notice: Subject to any disclaimer, the term of this patent is extended or adjusted under 35 U.S.C. 154(b) by 0 days.

(21) Appl. No.: 14/873,123

(22) Filed: Oct. 1, 2015

(65) Prior Publication Data

US 2016/0022287 A1    Jan. 28, 2016

Related U.S. Application Data

(63) Continuation of application No. 12/467,109, filed on May 15, 2009, now abandoned.

(51) Int. Cl.
   *A61B 17/16*    (2006.01)
   *A61B 17/17*    (2006.01)

(52) U.S. Cl.
   CPC ............................. *A61B 17/1757* (2013.01)

(58) Field of Classification Search
   None
   See application file for complete search history.

(56) References Cited

U.S. PATENT DOCUMENTS

| | | | | |
|---|---|---|---|---|
| 5,354,299 A | * | 10/1994 | Coleman ............ | A61B 17/1615 606/916 |
| 2007/0005072 A1 | * | 1/2007 | Castillo ............. | A61B 17/1671 606/79 |
| 2009/0014011 A1 | * | 1/2009 | Edlauer ............... | A61B 19/203 128/845 |

* cited by examiner

*Primary Examiner* — Samuel Hanna
(74) *Attorney, Agent, or Firm* — Baumgartner Patent Law;

(57) ABSTRACT

Temporary, radiographically opaque, bone markers having first and second penetration members that are concentric with one another and are configured to pierce bone are provided herein. Bone markers can non-exclusively be used to help verify the correct surgical site along the vertebrae, locate the vertical midline, and as a fixed point for aligning surgical instruments. Insertion and extraction devices for use with the bone markers are also provided herein.

18 Claims, 6 Drawing Sheets

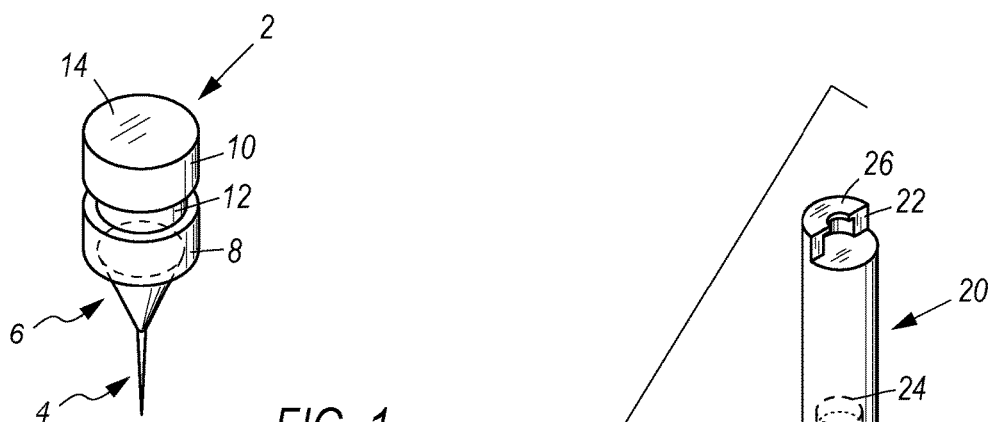
FIG. 1
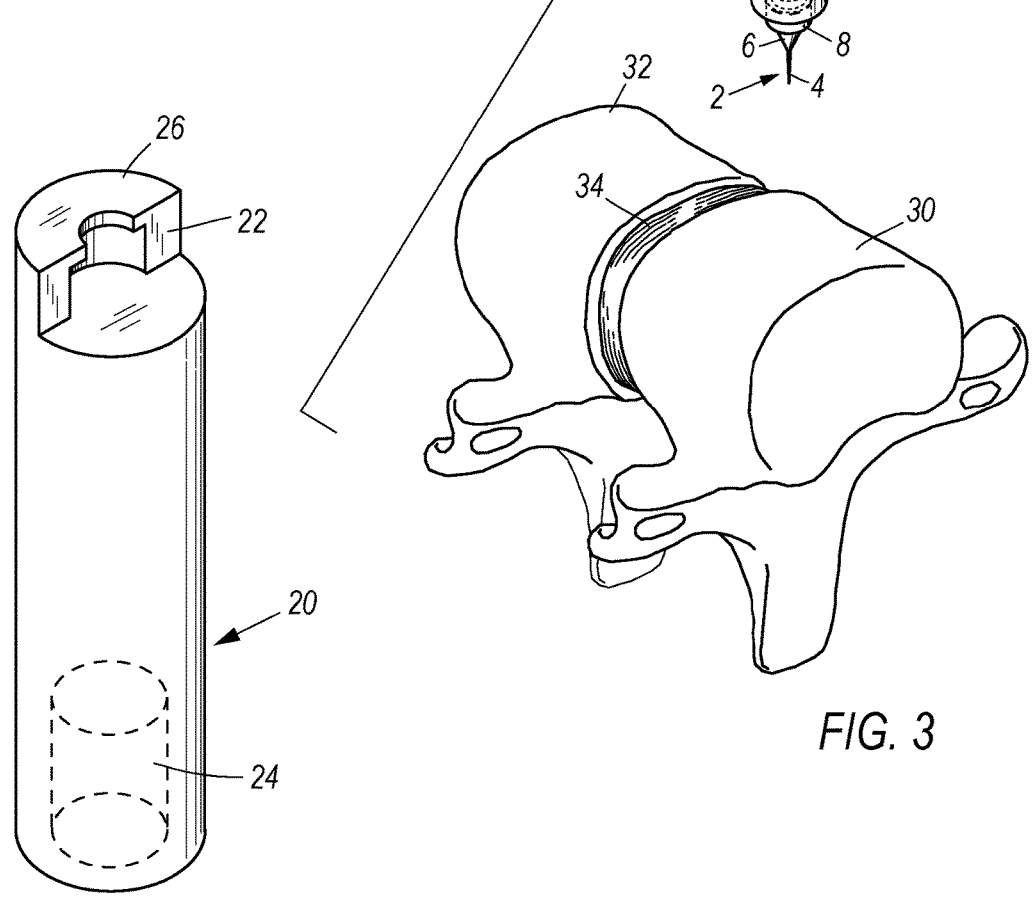
FIG. 2
FIG. 3

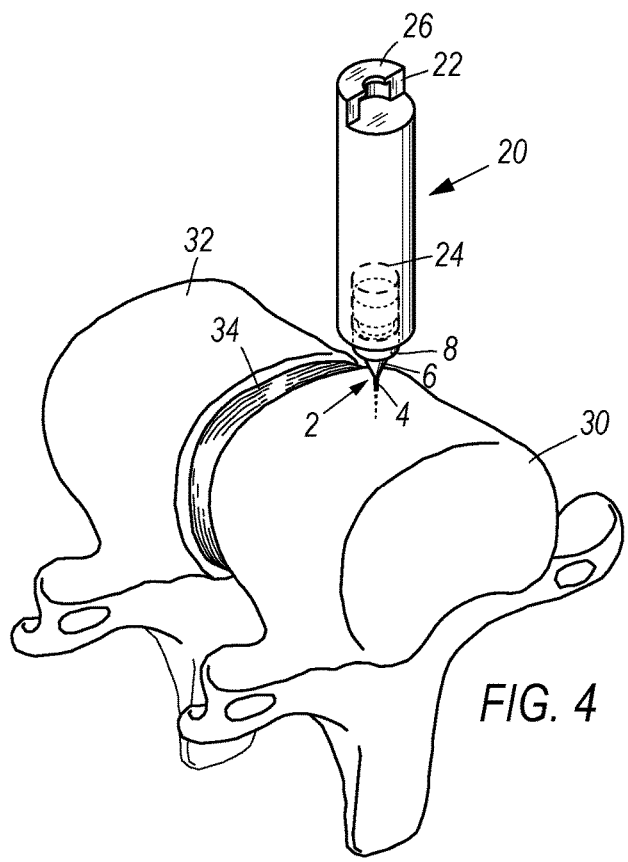
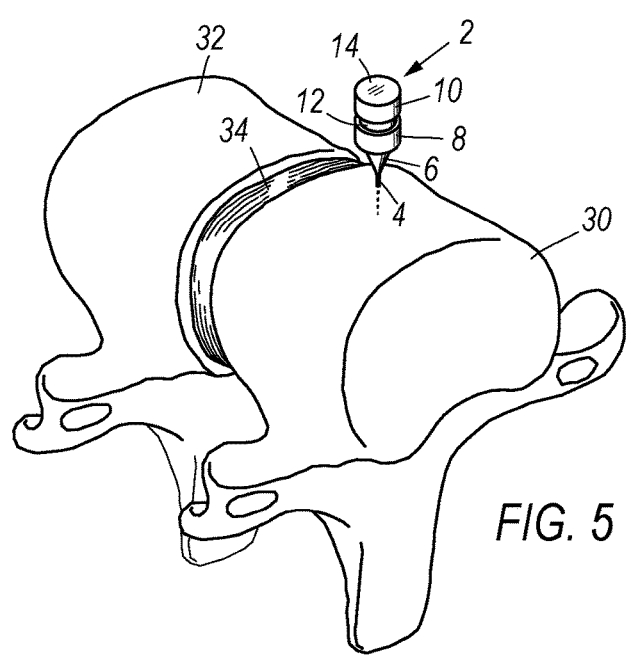
FIG. 4
FIG. 5

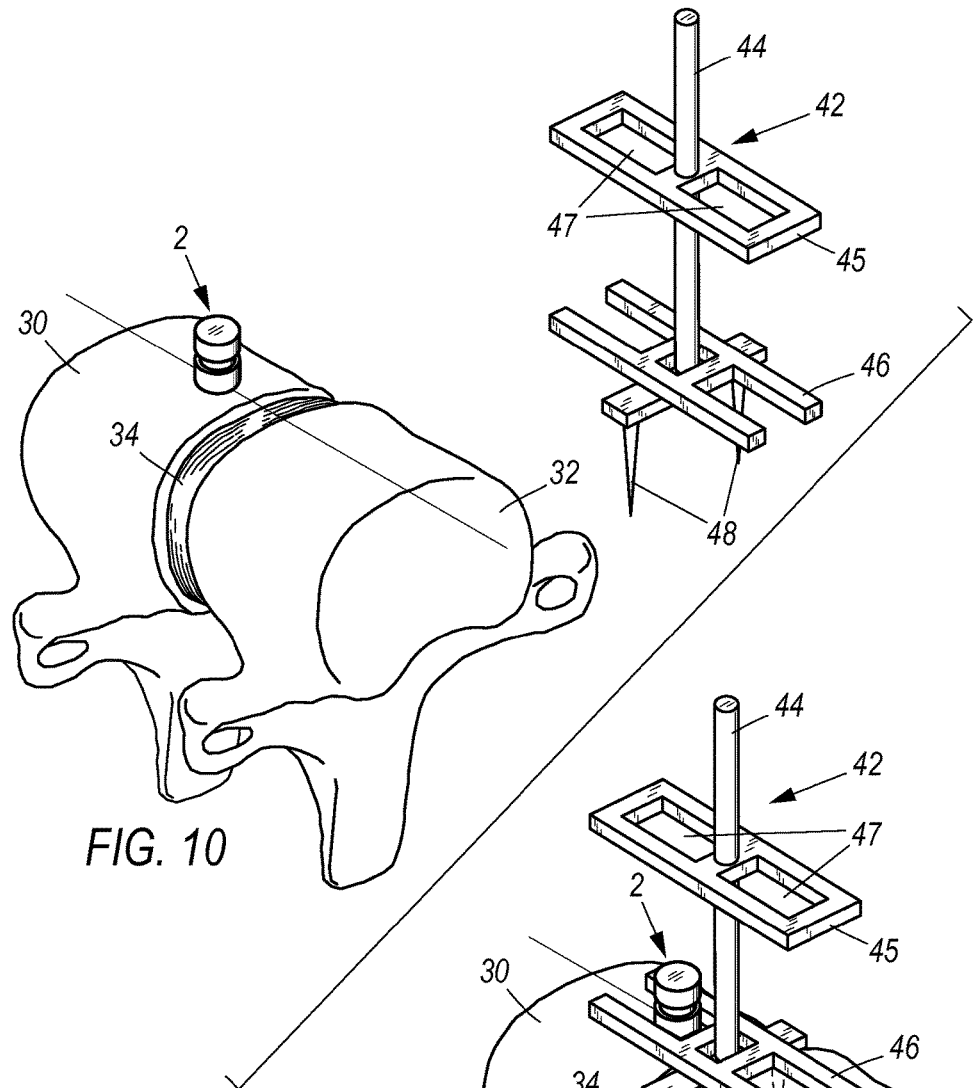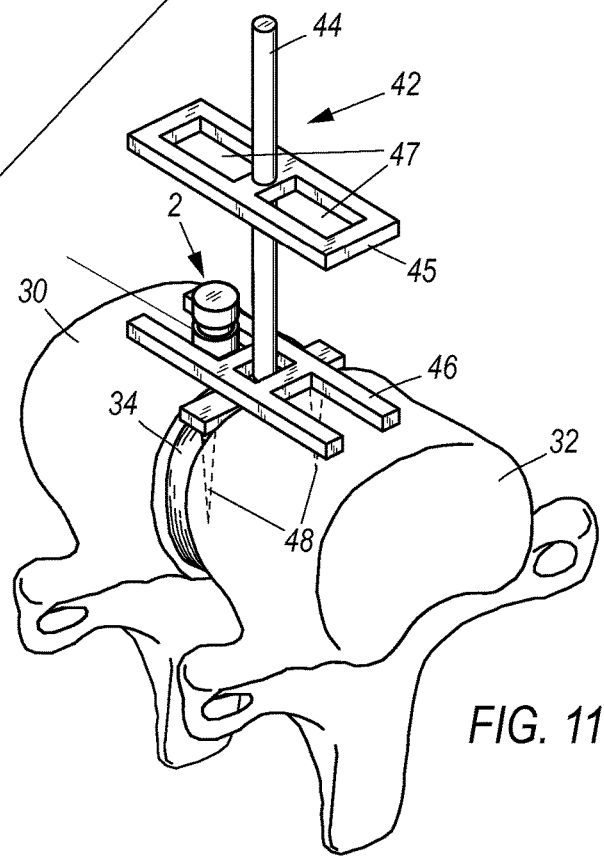
FIG. 10
FIG. 11

SPINAL MARKER SYSTEM AND METHODS OF USE

CROSS-REFERENCE TO RELATED APPLICATIONS

This application claims priority to and is a continuation to non-provisional U.S. Non-Provisional application Ser. No. 12/467,109 filed May 15, 2009, which is hereby expressly incorporated by reference in its entirety.

FIELD OF THE INVENTION

The embodiments herein relate to systems and methods useful in the medical field and are directed to temporarily marking the vertebrae in a patient in need. The assemblies and methods herein have many applicable uses including the ability to allow a surgeon to radiographically determine the location of a particular vertebral body. Additionally, the teachings herein can be used to locate a patient's vertebral midline, which is a useful determination for a variety of surgical procedures, non-exclusively including corpectomies and disectomies, for example.

BACKGROUND

When removing a disc from the spinal column, it is common practice for a surgeon to place a radiographically opaque needle into the exposed, potentially damaged disc and then view the needle via X-ray to ensure that the marked disc's location signifies that it is actually the damaged disc that is intended to be removed. Determining the location is often done by counting the vertebral bodies until the medical provider reaches the needled disc.

Unfortunately there are many problems associated with this practice. One such problem is that surgeons often puncture the wrong disc with the needle. This is understandably a common problem as the reason for using the needle is to verify whether the needled disc is in fact the damaged disc as opposed to a nearby healthy disc. Puncturing a healthy disc is undesirable in itself, but even more so when the needle pierces too far into the disc. While some have attempted to prevent over-piercing by using guards (See U.S. Pat. No. 5,195,526 to Michelson, hereinafter "Michelson I", for example) the art does not appear to recognize that inserting marking devices into a healthy disc area is deleterious in itself, whether or not there is "over penetration." Accordingly, there is a need to provide a system and method for radiographically determining the position of a damaged disc without potentially puncturing a healthy disc.

In addition to determining the position of an unhealthy disc, it is often also advantageous to use a marking system in order to determine the vertebral midline for proper graft, cage, and/or artificial disc implantation. Unfortunately, current systems and methods for determining the vertebral midline often involve piercing the disc space. See U.S. Pat. No. 6,224,607 to Michelson, hereinafter "Michelson II", for example. This is disadvantageous for the same reasons as discussed above.

Marking systems used to determine the alignment of the vertebral midline or to ascertain whether a penetrated disc is damaged also overly rely on dyes for injecting into the disc space. The use of dye requires unnecessary steps in spinal marking that are more expensive, time consuming, requires a cannulated marker, and allows for more human error in the marking procedure.

A further disadvantage of current marking systems is that they are only used to mark the disc area, not to created additional, larger holes for other instruments used in spinal surgery.

Based on the above described problems, an objective of the teachings herein is to provide improved systems and methods for spinal marking that allow the operating surgeon to both identify the position of the damaged disc targeted for removal and to ascertain the position of the vertebral midline to allow for aligned implantation after removal of the damaged disc, or portions thereof. It is a further objective of the embodiments herein to provide a spinal marking system that does not rely on dyes or cannulated marking systems. Further objectives of the markers provided herein are to act as a designated point upon which a surgical instrument, such as a drill guide, can operably couple with to obtain proper alignment.

SUMMARY OF THE INVENTION

Embodiments herein are directed to temporary surgical markers having a first penetration member having an apex configured to pierce bone, and a base that is concentric and operably coupled to an apex of a second penetration member configured to pierce bone, and having a larger cross-sectional body than the first penetration member. Preferred markers are made entirely or in part of a radiographically opaque material. If the markers are not entirely made of a radiographically opaque material, it is preferred that at least the first penetration member is. More specifically, the first penetration member can be radiographically opaque and the remaining marker can be radiographically lucent.

Preferably, the second penetration member includes a base operably coupled to a guard having a larger cross-section than the base. Preferred markers include a groove, such as an annular groove, positioned between the guard and an upper section of the marker. Advantageously neither the first nor the second penetration member include a cannula and are not suitable to transmit dye to the spine area. Preferred markers are configured to align the placement of a surgical instrument when embedded in bone.

Preferred embodiments are also directed to kits for marking a bone that include a temporary surgical marker comprising a first penetration member having a main body, an apex configured to pierce bone, and a base that is concentric and operably coupled to an apex of a second penetration member configured to pierce bone and having a larger cross-sectional body than the first penetration member; and an insertion device comprising means for releasably housing said surgical marker such that said first and second penetration members are exposed.

Preferably, the means for releasably housing the surgical marker comprise a release lever having a latch configured to operably couple to the groove. Advantageous insertion devices can further comprise means for extracting the marker when its first or second penetration member is embedded into bone. Said means for extracting the marker can include a flange configured to operably couple to the groove. Preferably, neither the first nor the second penetration member comprises a cannula.

BRIEF DESCRIPTION OF THE DRAWINGS

It will be appreciated that the drawings are not necessarily to scale, with emphasis instead being placed on illustrating the various aspects and features of embodiments of the invention, in which:

FIG. 1 is a perspective view of a marker

FIG. 2 is a perspective view of marker insertion device

FIG. 3 is a perspective view of the insertion device releasably coupled to a marker for insertion into a vertebral body FIG. 4 is a perspective view of the marker being partially inserted into a vertebral body FIG. 5 is a perspective view of the marker partially inserted into a vertebral body.

FIG. 10 is a perspective view of a drill guide.

FIG. 11 is a perspective view of the inserted marker being used to align the drill guide.

DETAILED DESCRIPTION OF THE ILLUSTRATED EMBODIMENTS

Figure 6:
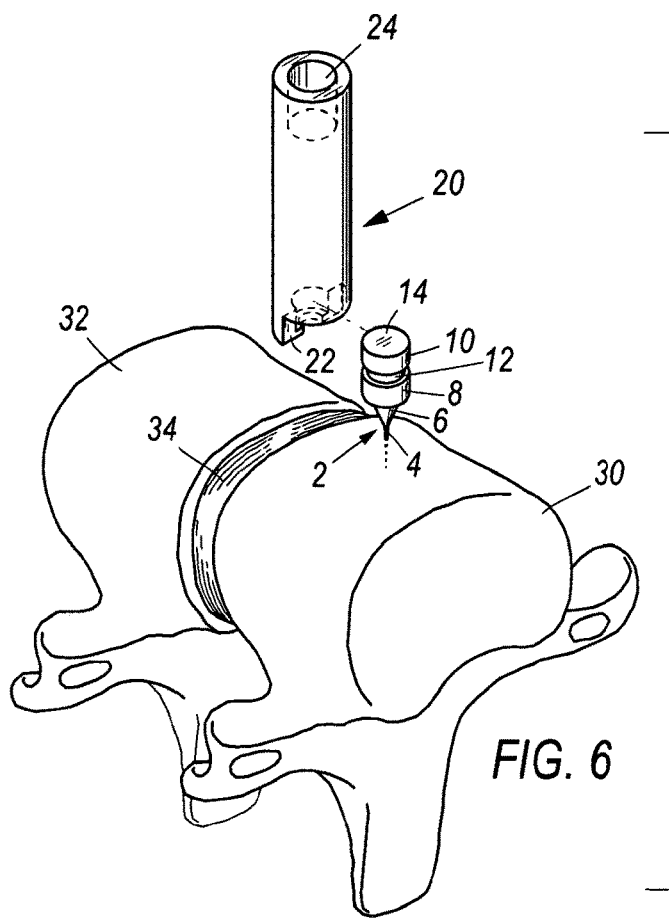
FIG. 6 is a perspective view of the marker being removed from the vertebral body
Figure 7:
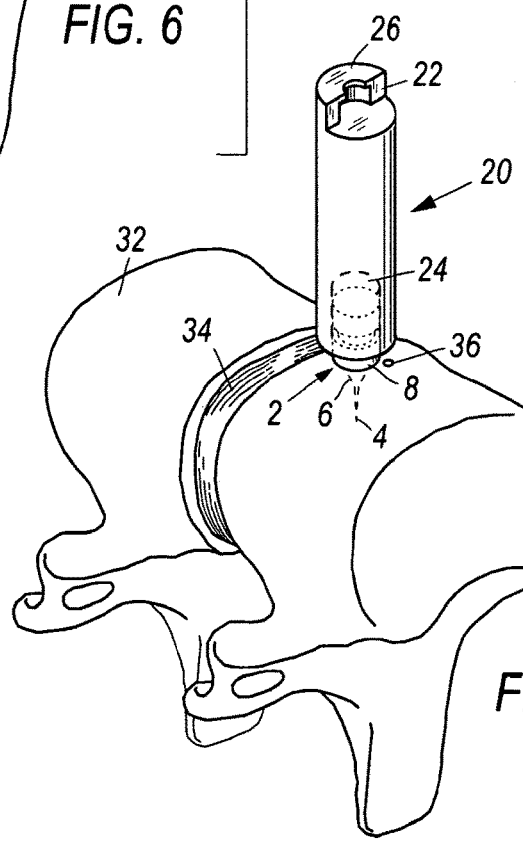
FIG. 7 is a perspective view of the marker being fully inserted into the vertebral body
Figures 8, 9:
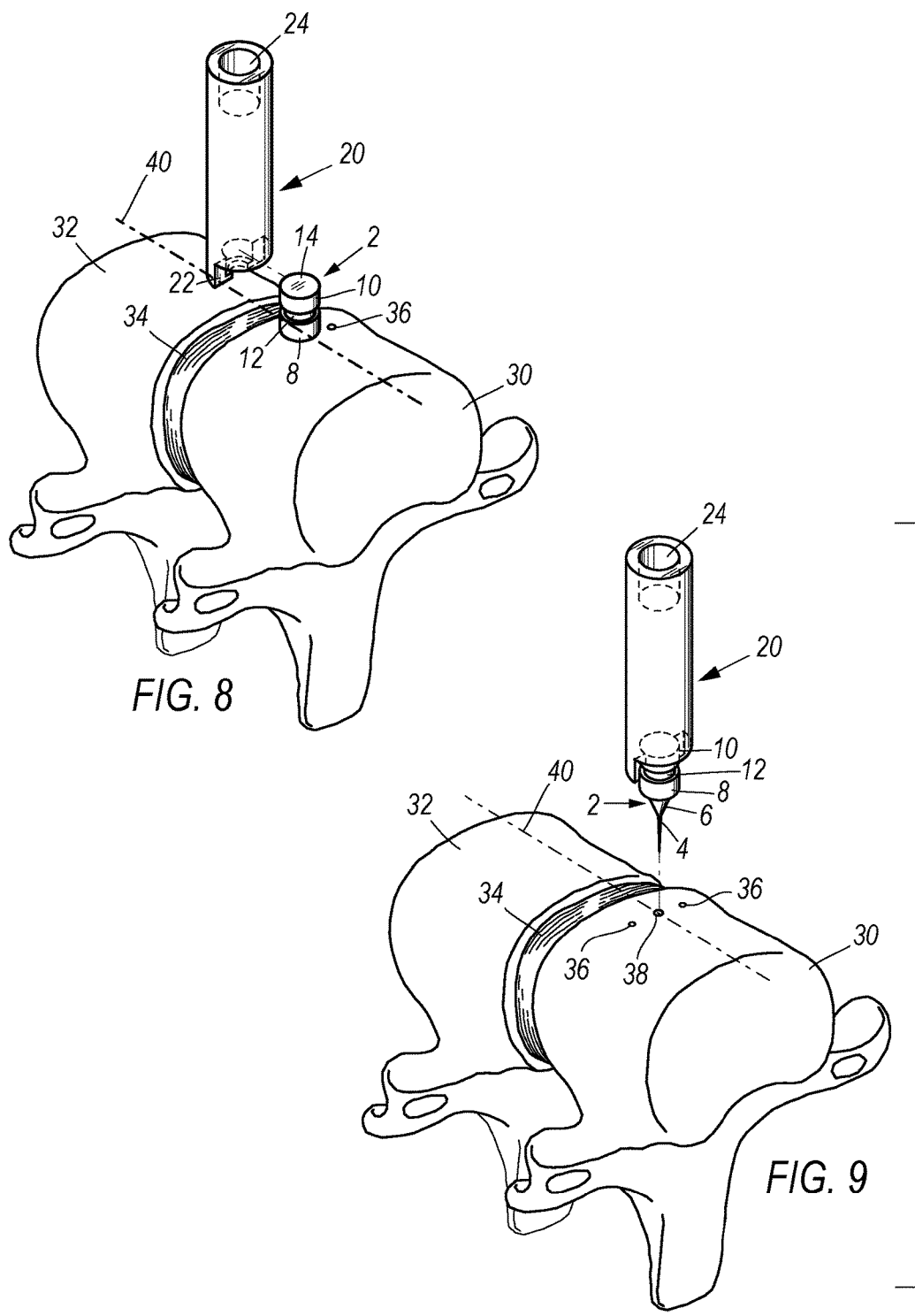
FIG. 8 is a perspective view of the fully inserted marker being extracted from the vertebral body
FIG. 9 is a perspective view of the larger hole in the vertebral body created after the fully inserted marker is removed.

Embodiments of the present invention are described below. It is, however, expressly noted that the present invention is not limited to these embodiments, but rather the intention is that modifications that are apparent to the person skilled in the art and equivalents thereof are also included.

FIG. 1 depicts an example of a marker 2 that can be used with the systems and methods herein. The bottom portion of the marker 2 preferably includes a first penetrating member 4 that includes a downward facing sharp point, or apex, configured to pierce a patient's vertebral body 30. The first penetrating member 4 is preferably in the shape of a needle or a narrow, inverted cone. Advantageously, the apex of the first penetrating member 4 is configured to make a small test hole 36 in the vertebral body 30 when pressed in. Preferably, the first penetrating member 4 includes a base positioned at the opposite end of the apex that is coupled to or traverses through the apex of a second penetrating member 6. According to even more preferred embodiments, the first and second penetrating members 4 and 6 are concentric with respect to each other.

Preferably the second penetrating member 6 is in the shape of an inverted wide cone, frustum, or pyramid and has a larger diameter than the first penetrating member 4, or is otherwise configured to make a larger hole 38 in the vertebral body 30, compared to the hole 36 made by the first penetrating member 4. More preferably the second penetrating member 6 is a right circular cone. While the second penetration member 6 can have a smooth outer surface, or substantially so, in other embodiments the second penetrating member 6 can include grooves and/or protrusions (not shown). These grooves or protrusions can traverse the slant height of the second penetrating member 6, or be otherwise positioned to make distinct indentations in the vertebral body 30. These grooves and/or protrusions and their corresponding indentations in the vertebral body 30 can be customized for various instruments or implants designed to be inserted into the hole left by the second penetrating member 6. Such surgical instruments or implants can include, distractor/retractor pins, and pins for aligning fusion plates or templates, for example. The first and second penetrating members 4 and 6 are each preferably between 2-3.5 mm in length, or 2.5-3 mm in length, or 2.79 mm, or approximately so, in length.

According to more specific embodiments, preferred markers 2 can include a guard 8 positioned above and operably coupled to the base of the second penetrating member 6. Advantageously the guard 8 prevents the second penetrating member 6 from inadvertently penetrating too deep into the vertebral body 30. Preferred guards 8 can be a variety of shapes (e.g., cylindrical, tapered, spherical, disc) and configurations, but include a larger cross-section (e.g., diameter) than the base of the second penetrating member 6. Preferred guards 8 are relatively thick to prevent bending by the marker 2. Guards 8 can advantageously be between 1-2 mm thick, or between 1.25-1.75 mm thick, or 1.55 mm thick, or substantially so.

Preferably, the markers 2 provided herein also include a groove 12 positioned above the guard 8 and below an upper section 10. More preferably, the groove 12 can be an annular groove, or semi-annular, or partially annular. The groove 12 can be used with a corresponding tool to facilitate the extraction and/or implantation of the marker 2 from or into the vertebral body 30. In certain embodiments, grooves can have heights between 1.5-2.5 mm, 1.75 and 2.25 mm, or 2.01 mm, or substantially so. The upper section 10 is positioned above the groove 12 and has a larger diameter than the groove 12. The diameter of the upper section 10 can be the same or similar size as the diameter of the guard 8, and can be configured to a variety of suitable shapes (e.g., cylindrical, tapered, spherical, or disc). The upper section 10 can include a top side 14 surface that can be readily detected by a viewer after anterior/posterior imaging (e.g., X-ray). The height of the upper section 10 can be between 1.75-3.25 mm, 2-3 mm, or 2.55 mm or substantially so.

Figure 12:
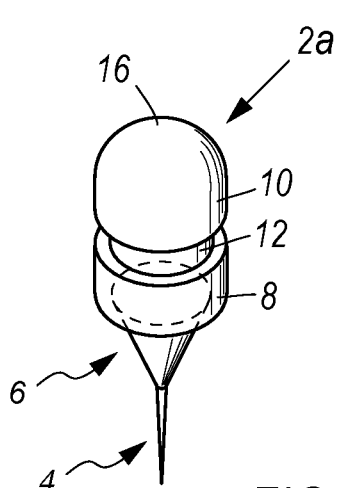
FIG. 12 is a perspective view of an alternative marker shape.

A second embodiment of marker 2a is depicted in FIG. 12 and is essentially the same as the first marker 2, depicted in FIG. 1 and described above, with the exception of having a rounded top side 16 instead of a substantially planar top side 14. The usage of the term "marker" herein, regardless of the reference number associated with the term, is expressly contemplated to include both embodiments of markers 2 and 2a.

Preferred markers 2 are low profile and have heights from the tip of the first penetrating member to the top of the marker that can be less than the following values: 2 cm, 1.5 cm, or 1 cm. Preferred markers have a height range between 0.5-1.5 cm, or between 0.8-1.3 cm, or a total height of 11.69 mm, or approximately so. The low profile is an advantageous design as it prevents the bending of the marker 2. Additional embodiments are directed to markers 2 that are not cannulated, and thus do not rely on guide wires or dyes. More specifically, according to these embodiments, neither the first nor second penetrating members 4 and 6 require a centrally located cannula that traverses to the apex of the first penetrating member, as they do not rely on syringes, inserting dyes into the disc space, or guide wires for insertion.

According to preferred embodiments, the markers 2 provided herein are entirely or partially radiographically opaque and are preferably made of metal, such as stainless steel, or titanium, for example. If the marker is partially radiographically opaque, it is preferred that at least the first penetrating member is radiographically opaque. The remaining part of the marker can be radiolucent.

Figure 13:
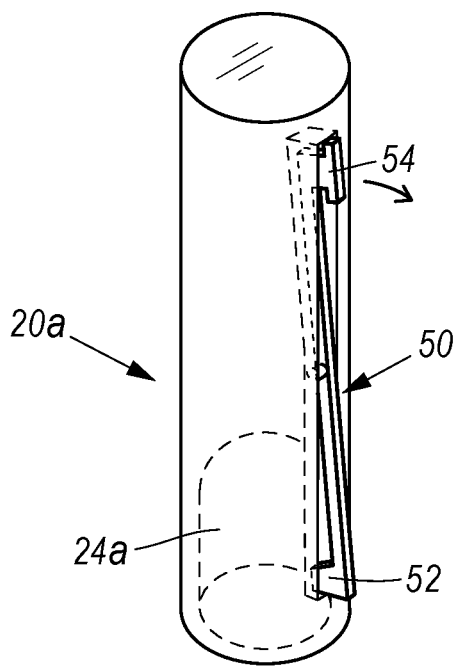
FIG. 13 is a perspective view of an alternative insertion device with a release lever in the open position.

A first embodiment insertion device 20 is shown in FIG. 2. Preferably, the inserter 20 includes means for inserting the marker 2. One example of a means for inserting the marker 2 is a cavity 24 positioned within the bottom end of the inserter 20 and that is configured to house the guard 8, groove 12, and upper section 10 of the marker 2 while leaving the first and second penetrating members 4 and 6 exposed for piercing the vertebrae 30. Alternatively, the cavity can additionally be opened on the lateral side of the insertion device such that the guard 8, groove 12 and upper section 10 of the marker 2 are partially exposed. While the cavity 24 can be cylindrical in shape, alternative shapes of cavities can be used depending on the specific shape of the marker used. For example, FIG. 13 depicts a second embodiment of insertion device 20a having a rounded cavity 24a (e.g., pill shaped or semi-pill shaped) to house a marker 2a having a rounded top 16.

The means for inserting the marker 2 allow the operating surgeon to apply downward pressure onto the insertion device 20 coupled to the marker 2 such as to be able to push said first penetrating member 4 or second penetrating member 6 into the vertebrae 30. More specifically, when the surgeon applies a first amount of pressure, the first penetrating member 6 will pierce the vertebrae 30 and create a small test hole 36. If the surgeon then applies a second amount of pressure, greater than the first, the second penetrating member 8 can pierce the vertebral body 30 and create a larger hole 38.

Preferred markers 2 can be configured to allow the first penetration member 4 to be relatively easily pushed into the vertebral body 30 while the second penetration member 6 can be configured to require more force to penetrate the vertebrae 30 as it is not as sharp as the first penetration member 4. Preferably, the cross-sectional perimeter of the second penetration member 6 is larger than the cross-sectional perimeter of the first penetration member 4, and shaped such that it gradually increases from its bottom end to top end. Because of the larger perimeter, the second penetration member 6 will require additional force to insert it into the vertebral body 30 beyond that required for insertion of the first penetration member 4. By controlling the downward pressure on the marker 2, the surgeon can choose whether the second penetration member 6 is pressed into the vertebrae 30 and the amount of penetration.

Figure 14:
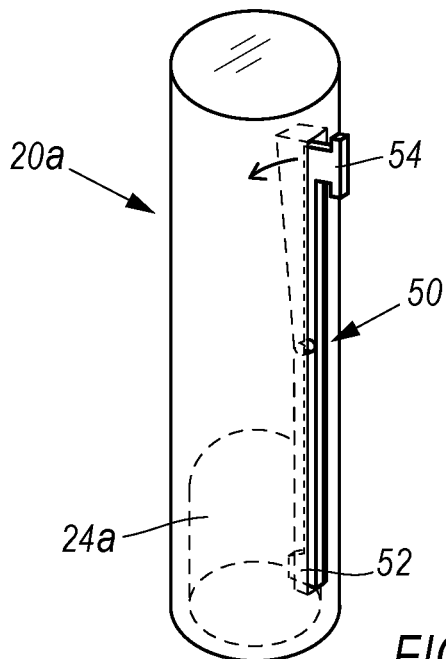
FIG. 14 is a perspective view of an alternative insertion device with a release lever in the closed, natural position.

The marker 2 can be held in its' cavity 24 by a light magnet or through any suitable release lever. One example of a release lever 50 is depicted in FIGS. 13 and 14. The release lever 50 preferably includes a release button 54 that when pushed releases a latch 52 configured to fit within the groove 12 of the marker 2a (FIG. 13). Preferably, when the release button 54 is in its natural state (FIG. 14), the latch 52 holds the marker 2a within the cavity 24a of the insertion device 20a. In other embodiments, the release lever 50 can also be used to extract the marker 2a when imbedded in the vertebrae 30. Advantageously, a second release lever (not shown) can be used with a first release lever such that two latches grip the groove 12 of the embedded marker 2a. Alternatively, the second insertion device 20a can include a flange (e.g., annular or semi-annular) on its end opposite from the insertion cavity 24a configured to fit within the groove 12 for extracting an embedded marker 2a.

Other insertion means for the markers 2 provided herein non-exclusively include screwdrivers, electric screwdrivers, mallets, or wrenches for markers with corresponding modified heads (e.g., Phillips, hex, or flat).

Preferred insertion devices 20 can preferably include means for removing the marker 2 from the vertebral body 30. Referring to FIG. 2, the top end of the inserter 20 includes means for removing a marker 2 having either its first or second penetration member 4 or 6 imbedded into the vertebral body 30. The means for removal can be any suitable means that couple to the marker 2 and allow the surgeon to pull the first or second penetrating member 4 or 6 out from the vertebral body 30. FIG. 2. depicts a means for removal that includes an elevated member 22 supporting a flange 26 in the shape of a semi-circle (or is otherwise arched) and is configured for coupling to the groove 12 on the marker 2. Once coupled to the groove 12, the flange 26 catches against the upper section 10 of the marker 2 and allows the surgeon to lift out either the first or second penetrating members 4 or 6 from the vertebrae 30. Another non-exclusive means for extracting the embedded marker 2 can include a cavity that opens on the lateral side of the insertion device that include one or more flanges configured to couple to the groove 12.

Other non-exclusive means for removing an embedded marker 2 can include one or more of the following members: clamp, retractable flange, or pliers, for example. These means can be separate from the insertion device 20 or alternatively coupled to it.

Preferred methods of using the markers 2 described herein are also contemplated. One preferred method is to use the markers 2 to test and verify which particular vertebral body or bodies (e.g., C5, C6, and C7) are exposed at the surgical site. Before exposing the vertebral area targeted to be operated on, the surgeon typically estimates externally where the targeted site on the patient is. Once the opening cut has been made and the spinal area is exposed, a surgeon should verify that the exposed site is indeed the targeted site for surgery.

As shown in FIGS. 3-9, the first penetrating member 4 can be used to make a first, test hole 36 in an exposed vertebral body 30 and the second penetrating member 6 can be used to make a final hole 38 in the vertebral body 30.

As exemplified in FIGS. 3 and 4, a surgeon can embed a marker's first penetration member 4 into the exposed vertebrae 30. After embedding the first penetration member 4 into the vertebral body 30, the insertion device 20 is disengaged from the marker 2 as shown in FIG. 5. The position of the marker 2 with the embedded first penetration member 4 can then be verified using an X-ray, or other available imaging tools. For example, an anterior/posterior and/or lateral X-ray can be taken showing the marker 2 embedded in the vertebral body 30 and more preferably, one or more unmarked vertebral bodies (e.g., such as the adjacent vertebral body 32) in the patient's spine. Reviewing the X-ray, the surgeon can determine which specific vertebral body 30 is marked by counting vertebral bodies from a known vertebral body to verify that the correct surgical site in the spine is marked. The C1 vertebral body on the X-ray, for example, can be used as a starting point for counting to the marked vertebral body 30. Additionally, the surgeon can review the anterior/posterior X-ray to verify that the marker 2 is positioned along the vertebral midline 40 if so desired.

If the X-rayed marker's 2 test position is in the incorrect vertebral body or in the wrong position on the correct vertebral body (e.g., not along the vertebral midline 40), the marker 2 can be removed using means for extraction as shown in FIG. 6, and a new test hole at another location on the same vertebral body 30 or into a different vertebral body 32 can be made. The position of the second and subsequent test positions can again be verified by X-ray. Once the desired location has been obtained with the first penetrating member 4, the marker 2 can be pressed further into the vertebral body 30 such that the second penetrating member 6 makes a larger hole 38 in the vertebral body 30. The embedding of the second penetration member 6 is exemplified in FIG. 7. Determining whether the first penetration member 4 of the marker 2 is pressed into the correct location before pressing the second penetrating member 6 into the vertebrae 30 can be ascertained in a variety of ways, non-exclusively including, directly viewing the site, a lateral X-ray view, or anterior/posterior X-ray view, for example.

According to preferred embodiments, the larger hole 38 can be used either as a better target and/or a location to position other surgical instrumentation, such as distraction pins, for example. Advantageously, the systems and methods provided herein allow the surgeon to first create smaller test holes 36 in the vertebral body until the desired position is obtained, and then a larger hole 38 can be made. According to certain embodiments, the second penetrating member 6 does not include an entirely smooth outer surface, but can includes protrusions or indentations that are configured to make specialized holes in the vertebral body 30 to accommodate various instruments or implants, such as distractor/retractor pins, or drill guides, for example. According to the teachings herein, it is highly advantageous to have a single marker 2 configured to have the ability to make both a smaller test hole(s) 36 and larger hole(s) 38 in a vertebral body 30.

Additional embodiments are directed to methods of using the markers 2 herein as fixed points for aligning surgical instrumentation. One example of these methods is exemplified in FIGS. 10 and 11. FIG. 10 depicts a drill guide 42 that can be aligned with the marker 2 embedded in the vertebrae 30. In this example, the drill guide 42 includes a handle 44 operably coupled to upper frame 45 comprising aiming ports 47 and a lower alignment guide 46 comprising a pair of parallel bars. The drill guide 42 is configured to be held in place by anchoring spikes 48 facing the patient's spine.

With reference to FIG. 11, the embedded mark 2 is configured to be straddled by the parallel bars of the alignment guide 46 and the anchoring spikes 48 pierce the disc space. Thus, the marker 2 can ensure the drill guide 42, or another surgical instrument, is aligned how the surgeon desires, such as along the vertebral midline 40, for example. Once the drill guide 42 is aligned and anchored, a surgeon can drill in the unmarked vertebrae 32 through one of the aiming ports 47, and between the parallel bars of the alignment guide 46. Additionally, the marker 2 can be extracted and the surgeon can guide a drill through one of the aiming ports 47 into the larger hole 38 created by the second penetration member 6. The drilled holes are preferably configured to set a distractor pin for separating the disc space between the vertebral bodies 30 and 32. The fixed distractor pins can in turn, be used to align a fusion plate or template. Alternatively, the distractor pins, or other types of instruments, can be secured directly (e.g., screwed) into the one or more larger holes 38 made in the vertebrae without a drill.

In other embodiments a second marker (not shown) can be placed in the same or the adjacent vertebrae 32 such that there are two fixed points for the alignment guide 46 bars to straddle and/or two holes for instruments to be secured into.

The invention may be embodied in other specific forms besides and beyond those described herein. The foregoing embodiments are therefore to be considered in all respects illustrative rather than limiting, and the scope of the invention is defined and limited only by the appended claims and their equivalents, rather than by the foregoing description. All references provided herein are expressly incorporated by reference in their entireties.

The invention claimed is:

1. A method of temporarily marking a target site on a vertebral body in a patient in need for a surgical procedure, said method comprising:
   providing a spinal marker comprising:
   a first penetration member having a first apex configured to pierce a bone of the vertebral body that forms a first taper from a first base;
   a second penetration member having a second apex configured to pierce the bone, that forms a second taper with a second base, such that the second taper is non-linear with and steeper than the first taper;
   wherein the first base of the first penetration member is concentretic to, abuts to, and does not have a larger cross-section than the second apex of the second penetration member where the first base and the second apex abut;
   estimating a location of the target site within the patient;
   exposing a first vertebral body of the patient;
   inserting the first apex of the first penetration member of the marker into the bone of the anterior face of the first vertebral body to make a first test hole;
   imaging the first vertebral body to verify the position of the first penetration member of the spinal marker embedded in the first vertebral body, using a radiographic imaging tool to generate a first image, is at the target site;
   reviewing said image and verifying the position of the first penetration member of the spinal marker embedded in the first vertebral body relative to the actual target site;
   wherein when the position of the inserted first penetration member of the spinal marker on the image is not verified at the actual target site, extracting the spinal marker from the first test hole in the first vertebral body and re-inserting the first apex of the first penetration member into a different position from the first test hole within the bone of the anterior face of the first vertebral body or the bone of the anterior face of a second vertebral body of the patient to make a second test hole; and then repeat the step of the imaging the first or second vertebral body, using the radiographic imaging tool to generate a second image, to verify the different position of the first penetration member of the spinal marker embedded in the first or second vertebral body is at the target site on the second image;
   wherein when the position of the inserted first penetration member of the spinal marker on the first or second image is verified to be at the actual target site, inserting the spinal marker further into the first or second test hole in the bone of the anterior face of the first or second vertebral body, such that the second penetration member embeds within the bone of the first or second vertebral body and creates a second final hole larger than, and concentric to, the first or second test hole; and removing the spinal marker from the target site.

2. The method of claim 1, wherein a vertebral midline in the patient is verified by the radiographic imaging after insertion of the first penetration member into the target site and before insertion of the second penetration member into the target site.

3. The method of claim 1, wherein the position of a target vertebral disc relative to non-targeted discs is ascertained by the radiographic imaging.

4. The method of claim 1, further comprising using the spinal marker to align the placement of a surgical instrument when the second penetration member is embedded in bone, before the spinal marker is removed from the patient's target site.

5. The method of claim 4, wherein the surgical instrument is a drill guide.

6. The method of claim 5, wherein the drill guide has parallel bars that straddle the spinal marker.

7. The method of claim 1, wherein the first and second test holes are only made within the first vertebral body of the patient.

8. The method of claim 1, wherein the first and second test holes are respectively made within the first and second vertebral bodies of the patient.

9. The method of claim 1, wherein a distractor pin is positioned within the second final larger hole, after the spinal marker is removed from the patient's target site.

10. The method of claim 1, wherein the spinal marker further comprises a guard that abuts to and has a larger cross-section than the second base of the second penetration member where the guard and the second base abuts.

11. The method of claim 10, further comprising a groove positioned between the guard and an upper section of the marker, wherein the groove has a smaller cross-section than the guard and the upper section.

12. The method of claim 11, wherein the groove is an annular groove.

13. The method of claim 11, wherein the first penetration member, second penetration member, and guard are of a monolithic construct.

14. The method of claim 1, wherein the first base of the first penetration member entirely tapers to the apex of the first penetration member.

15. The method of claim 1, wherein the height of the marker has a height, as measured from the first apex of the first penetration member to a top side surface of the marker, which is between 0.5 to 1.5 cm.

16. The method of claim 1, wherein the outer surfaces of the first and second penetration members are smooth.

17. The method of claim 1, wherein the first and second penetration members lack a cannula traversing through them.

18. The method of claim 1, wherein the imaging of the marker is used to position a distraction pin into the target site.

* * * * *